United States Patent [19]
Johnson et al.

[11] 4,317,886
[45] Mar. 2, 1982

[54] MULTIPLE INTERIOR SURFACE ROLLER BOTTLE

[75] Inventors: Luther R. Johnson, Thousand Oaks; Bruno V. Sapatino, Oxnard, both of Calif.

[73] Assignee: Becton, Dickinson and Company, Paramus, N.J.

[21] Appl. No.: 176,936

[22] Filed: Aug. 11, 1980

[51] Int. Cl.³ .............................................. C12M 3/04
[52] U.S. Cl. .................................. 435/285; 435/240
[58] Field of Search ............... 435/284, 285, 286, 240, 435/241

[56] References Cited
U.S. PATENT DOCUMENTS 1,364,763  1/1921  Houghton .
3,314,563  4/1967  Mounier ................................. 215/6
3,827,943  8/1974  Mann ..................................... 435/285
3,853,712  12/1974 House et al. .......................... 435/285
3,856,138  12/1974 Maekawa et al. ................... 206/221
3,941,661  3/1976  Noteboom .......................... 435/285

Primary Examiner—Robert J. Warden
Attorney, Agent, or Firm—Richard J. Rodrick

[57] ABSTRACT

A roller bottle for cell growth culturing comprises an outer housing defining a hollow chamber therein. At least one annular member is inside the chamber spaced a short radial distance inwardly from the housing. The space between the annular member and the housing is in fluid communication with the chamber. The surfaces of the annular members and the interior surface of the housing are adapted to grow cells thereon.

12 Claims, 5 Drawing Figures

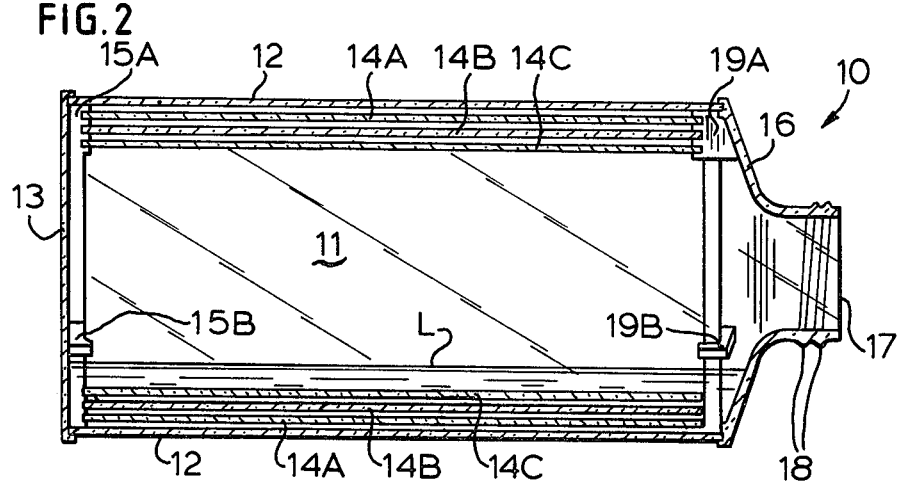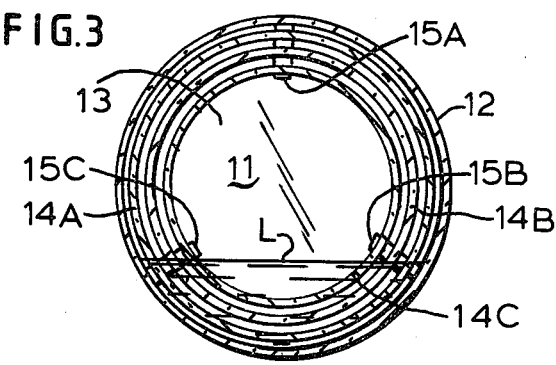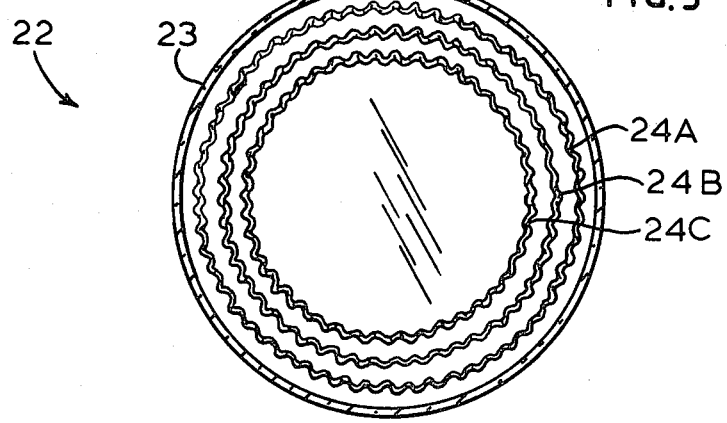

MULTIPLE INTERIOR SURFACE ROLLER BOTTLE

BACKGROUND OF THE INVENTION

The present invention relates to a roller bottle for cell growth production, and more particularly, concerns a roller bottle with multiple interior surfaces for cell growth culturing.

Certain larger containers which are used in the laboratory and like situations for culturing of cells are commonly known as "roller bottles." These roller bottles are generally cylindrically shaped and are adapted to rotate about their round peripheral surface. The interior surfaces of such roller bottles may be treated to provide active surfaces for the culturing of cells. When a liquid growth medium is introduced into the roller bottle, the rotating movement of the bottle keeps the interior surfaces wetted with the liquid medium thereby encouraging the growth of cells. Rotating rollers in an appropriate apparatus are employed to rotate these roller bottles. Many times the rotating apparatus is adapted to be placed inside an incubator or incubating room to control the temperature of cell growth inside the roller bottles.

Oftentimes in research, commercial or industrial laboratories it is necessary to grow large amounts of cells, mostly for cell by-products, such as pharmaceutical substances that are secreted by cells; for example, insulin, interferon, urokinase or viral vaccines. Standard roller bottles have been somewhat successful in increasing the yield of cell growth inasmuch as the entire inside peripheral surface area can be utilized for cell culturing.

In conceiving ways to increase the yield of growing cells in roller bottles, there are substantial constraints which have to be considered in suggesting improvements. In particular, roller bottle rotation apparatuses are widely used in standard sizes and incubators. These apparatuses are in place in many laboratories and are designed to accept roller bottles of a specific size and shape. To replace these rotational apparatuses would be expensive and cause substantial lack of standardization throughout the laboratory field. Thus, the outside configuration or diameter of roller bottles is generally not one of the parameters which would be disturbed in making improvements to standard roller bottles.

Moreover, in the fabrication of the roller bottles, the manufacturing processes place constraints on the overall longitudinal dimension of the bottle which can be formed. Taking into consideration the diameter of the bottle and the strength requirements which it needs to be selfsupporting, these kinds of roller bottles face a practical limitation in the overall length dimension. And, as mentioned above with respect to the roller bottle apparatus, even if fabrication technology would allow unlimited length formation, the bottles cannot be so long that they would not fit the standard type apparatus. Accordingly, improvements in roller bottles for increasing cell growth area, for practical purposes, would be generally limited to modifications of the interior surfaces of the roller bottle.

Various containers or bottles have been disclosed which include an interior compartment within an outer compartment or housing. These types of containers are typified in U.S. Pat. Nos. 3,856,138; 3,314,563; 1,364,763; and 714,968. The inventions disclosed in these patents are generally directed to multi-compartment containers generally adapted to form receptacles for holding several different kinds of liquids. However, the art of bottles, and roller bottles in particular, has not been known to teach the inclusion of a preferably concentric multi-interior surfaced roller bottle, such interior surfaces having been treated to have cell growth thereon. It is to such an improvement of the interior surfaces of a roller bottle for increasing the yield of cell growth that the present invention is directed.

SUMMARY OF THE INVENTION

A roller bottle for cell growth culturing comprises an outer housing defining a hollow chamber therein. At least one annular member is placed inside the chamber spaced a short radial distance inwardly from the housing. The space between the member and the housing is in fluid communication with the chamber. The surfaces of the member and the interior surface of the housing are adapted to grow cells thereon.

In a preferred embodiment of the present invention, the outer housing is substantially cylindrically shaped and is made of plastic, which may be translucent, and includes a liquid opening at one end. A plurality of plastic hollow tubes is positioned in the chamber spaced closely and concentrically to each other and to the interior surface of the housing. These tubes extend inside substantially the entire length of the housing and are connected to the housing by support clips mounted at opposite ends of the tubes. In between the tubes, the spaces are in fluid communication with the chamber; the inner and outer annular surfaces of each tube, in addition to the interior surface of the housing, are adapted to grow cells thereon. Preferably, these cell growing surfaces have been preliminarily and uniformly treated to enhance cell adhesion thereto.

In accordance with the principles of the present invention, the multiple interior surface roller bottle provides significantly greater area for cell growth and yield than standard roller bottles of the same external dimensions. At the same time, however, the roller bottle of the present invention may be used on standard roller apparatus and in standard incubators using the same procedures as standard roller bottles. As a result of the present invention, the harvesting of cells and cell products is made easier than known devices of similar cell growth surface area. In existing roller bottle cell production technology, the capacity is limited by the single wall surface area, the number of roller bottles which can be placed on the roller apparatus and the available incubator space. By greatly increasing the cell growth area without increasing the external dimensions of the bottle, the present invention will greatly increase the cell production capacity of existing equipment. These advantages and improvements are realized due to the structural features of the present invention which significantly increase the surface area for cell growth in roller bottles, without having to increase the quantity or size of roller apparatus, incubators or incubator rooms.

BRIEF DESCRIPTION OF THE DRAWINGS

FIG. 2 is a cross-sectional view taken along line 2—2 of FIG. 1;

FIG. 3 is a cross-sectional view taken along line 3—3 of FIG. 1;

FIG. 5 is a sectional view, similar to FIG. 3, of an alternate embodiment of the present invention with modified interior surfaces.

DETAILED DESCRIPTION

Figure 1:
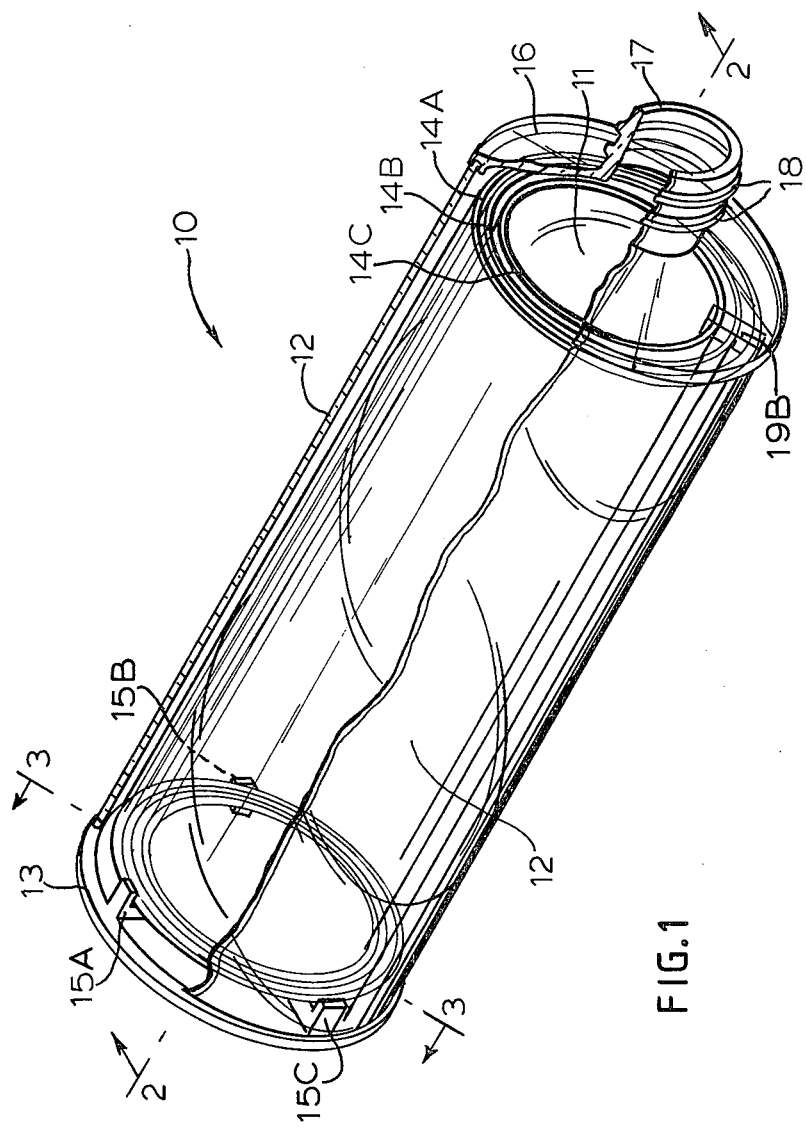
FIG. 1 is a perspective view of the preferred roller bottle of the present invention, partially broken away for viewing the interior thereof.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, particularly FIGS. 1, 2 and 3, there is illustrated the preferred embodiment of a multiple interior surface roller bottle 10 of the present invention. Roller bottle 10 includes an outer housing 12 which is preferably substantially cylindrically shaped, and is formed of a diameter to be acceptable on standard roller apparatuses for rotating roller bottles. Outer housing 12 is essentially a hollow tube which defines a hollow chamber 11 within. At one end of housing 12 a base 13 is connected to housing 12 in a liquid-tight attachment. This attachment may be made by any suitable means including adhesives, sonic welding and the like. Base 13 may, if desired, contain a recess (not shown) to permit nesting of roller bottles snugly on a roller apparatus.

Three inner concentric hollow tubes 14a, 14b and 14c are positioned in chamber 11 and are spaced closely to each other and to the interior surface of housing 12. Tubes 14 are preferably thin-walled structures which extend inside the roller bottle substantially the entire length of housing 12. These inner tubes are substantially rigid so as to be self-supporting under their own weight inside the housing. While three inner hollow tubes are described in conjunction with the present invention, it is appreciated that this number can be varied to suit different requirements for roller bottles. The inner and outer annular surfaces of each hollow tube and the interior surface of housing 12 are tissue culture treated either before assembly, when partially assembled or when fully assembled, thus providing for optimum tissue culture treatment. Preferably, these tissue culture treated surfaces are uniformly treated to enhance homogenous cell adhesion thereto. It is noted that each concentric tube 14a, 14b and 14c is only slightly smaller in diameter than its adjacent externally lying tube so that the surfaces of the tubes are arranged in close proximity to the interior surface of the housing. This arrangement is desirable because the liquid growth medium which is placed into the roller bottle generally fills the roller bottle only partially thereby providing a liquid surface only across a segment of the diameter of the bottle. This level of liquid is designated as L in FIG. 3; all of the concentric inner tubes should be covered by the level of liquid L during the time when the roller bottle is rotating so that all of the surfaces are in contact with the liquid growth medium therein, while maintaining liquid level L below the lower level of liquid opening 17.

At the end of roller bottle 10 opposite from base 13, a neck section 16 is provided which is sealably attached to housing 12 to form a liquid-tight connection. A liquid opening 17 is formed in neck section 16 and is preferably along the longitudinal axis of the roller bottle. Appropriate threads 18 are formed around opening 17 in order to accept a mating closure cap 20 (as seen by referring to FIG. 4). Cap 20 provides a liquid-tight closure around opening 17.

In order to hold inner tubes 14a, 14b and 14c in position inside the roller bottle, a number of clips 15 are provided at the base end of the tubes and similar clips 19 are provided at the neck end of the tubes. Specifically, clips 15a, 15b and 15c are substantially equally spaced around base 13 and include slots therein in a corresponding number to the number of inner tubes which are employed with the roller bottle. At the other end of the bottle, three substantially similar clips 19a, 19b and 19c are formed in and connected to neck section 16 and have the corresponding slots therein.

In assembling the roller bottle, clips 15, and outer housing 12 are connected to base 13 by appropriate fastening means, such as sonic welding, adhesives or the like. On the other hand, these components may be integrally formed as a molded unit if the materials are chosen which lend compatibility to the molding process. Inner tubes 14a, 14b and 14c are then inserted into the slots of support clips 15a, 15b and 15c in either press fit fashion or by permanent attachment, whereby adhesives could be used. Neck section 16 is then applied to the previously described composite structure so that the slots in support clips 19a, 19b and 19c are pressed over the ends of inner tubes 14a, 14b and 14c. The neck section is then permanently connected to outer housing 12 to provide a liquid-tight seal. It is appreciated that while three support clips 15 and 19 on the respective ends of the tubes are described, this number may be varied as long as the desired support of the inner tubes is accomplished. In other words, the inner tubes may be mounted inside the roller bottle without the specific type of support clips just described. For instance, the inner tubes may be directly adhesively fastened to the base and neck section during assembly of the roller bottle.

Also, support clips 15 and 19 on respective ends of the inner tubes are spaced apart so that the spacings between inner tubes 14a, 14b and 14c and the interior surface of housing 12 are in fluid communication with chamber 11. This allows liquid growth medium L to flow into these spacings therebetween to coat the growth treated surfaces during rotation of the roller bottle.

Figure 4:
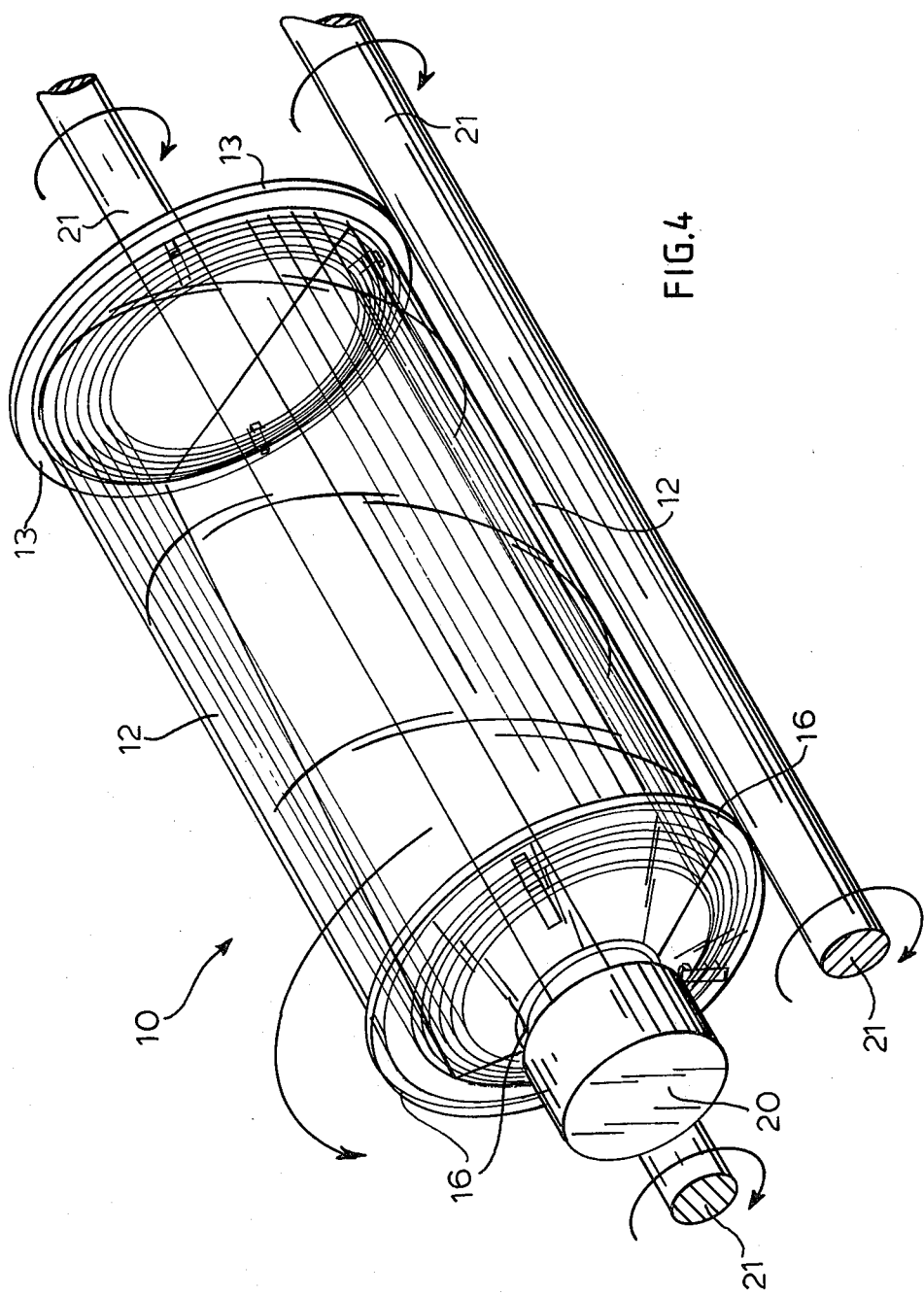
FIG. 4 is a perspective view of the roller bottle of FIG. 1 as it would appear on a standard roller apparatus.

This rotation is more clearly illustrated in FIG. 4 whereby rollers 21 are rotating with roller bottle 10 thereon being driven by the rollers. This type of rotation structure may be used in an incubator for temperature control of the cell culture process. Liquid growth medium L placed inside the roller bottle then is allowed to coat all of the interior surfaces inside the roller bottle which may have been treated to allow cell growth thereon. The rotating motion of the roller bottle causes the liquid growth medium to constantly wet the surfaces and encourage the growth of cells. It can be seen that the inner tubes significantly increase the surface area on which cells grow whereby the yield of cells is magnified substantially.

Surface area for cell culturing can be further increased by utilizing the embodiment illustrated in FIG. 5. In this embodiment, roller bottle 22 has an outer housing 23 substantially similar to the outer housing of the previously described embodiment. Base and neck sections are also similar. However, the inner hollow concentric tubes 24a, 24b and 24c are corrugated around their annular surfaces as illustrated in FIG. 5. Both inner and outer surfaces of these corrugated tubes are tissue culture treated to permit cells to attach and grow on both inner and outer surfaces of these tubes, the corrugation thereby providing a tremendous increase to the area available for growing cells inside this roller bottle.

While the roller bottle components may be made from many different materials compatible with cell growth production, it is preferred that all of the components be made of plastic.

Thus, the roller bottle of the present invention can be used with standard roller apparatus and incubators while it is constructed, arranged, treated and processed in a manner which provides significantly more cell growth area and yield than standard roller bottles of the some external dimensions.

What is claimed is:

1. A roller bottle for cell growth culturing comprising:
    an outer substantially cylindrical housing defining a hollow chamber within and includng a liquid opening therethrough; and
    a plurality of hollow discontinuous tubes positioned in said chamber and spaced substantially concentrically to each other and to the interior surface of said housing, the spaces between said tubes being in fluid communication with said chamber, the annular surfaces of said tubes and the interior surface of said housing adapted to grow cells thereon.

2. The roller bottle of claim 1 wherein said tubes extend inside substantially the entire length of said housing.

3. The roller bottle of claim 1 wherein said liquid opening is at one end of said housing located substantially on the longitudinal axis thereof.

4. The roller bottle of claim 1 wherein the inner and outer surfaces of each tube and the interior surface of said housing are uniformly treated to enhance cell adhesion.

5. The roller bottle of claim 1 wherein said tubes are connected to said housing by support clips located at opposite ends of said tubes.

6. The roller bottle of claim 1 wherein each concentric tube is only slightly smaller in diameter than its adjacent externally lying tube so that the surfaces of said tubes are arranged in close proximity to the interior surface of said housing.

7. The roller bottle of claim 1 wherein said tubes are corrugated around their annular surfaces to increase the surface area for growth of cells.

8. The roller bottle of claim 1 which includes a cap closure sealing said opening in liquid-tight engagement with said housing.

9. A roller bottle for cell growth culturing comprising an outer housing defining a hollow chamber therein and at least one discontinuous annular member inside said chamber spaced a short radial distance inwardly from said housing with said space therebetween being in fluid communication with said chamber, the surfaces of said member and the interior surface of said housing adapted to grow cells thereon.

10. The roller bottle of claim 1 or 9 wherein said housing and said tubes are made of plastic.

11. The roller bottle of claim 10 wherein said plastic is translucent.

12. A roller bottle for cell growth culturing comprising:
    an outer substantially cylindrical plastic housing defining a hollow chamber within and including a liquid opening at one end substantially on the longitudinal axis thereof; and
    a plurality of plastic hollow discontinuous tubes positioned in said chamber spaced closely and concentrically to each other and to the interior surface of said housing, said tubes extending inside substantially the entire length of said housing and connected to said housing by support clips mounted at opposite ends of said tubes, the spaces between said tubes being in fluid communication with said chamber, the inner and outer surfaces of each tube and the interior surface of said housing adapted to grow cells thereon and being uniformly treated to enhance cell adhesion thereto.

* * * * *